United States Patent [19]

George et al.

[11] 4,154,596
[45] May 15, 1979

[54] GIBBERELLIN SALTS

[75] Inventors: Edwin F. George, Basingstoke;
Jeffrey C. Lawrence, Crowthorne;
Michael R. Middleton, Reading, all of England

[73] Assignee: Imperial Chemical Industries Limited, London, England

[21] Appl. No.: 844,427

[22] Filed: Oct. 20, 1977

[30] Foreign Application Priority Data

Nov. 4, 1976 [GB] United Kingdom ............... 45922/76

[51] Int. Cl.$^2$ ................................................. A01N 9/12
[52] U.S. Cl. ............................................. 71/89; 71/88
[58] Field of Search ................................. 71/89, 117; 260/343.3 G

[56] References Cited

U.S. PATENT DOCUMENTS

| | | | |
|---|---|---|---|
| 3,118,753 | 1/1964 | Shive et al. | 71/89 |
| 3,137,562 | 6/1964 | Leben | 71/89 |
| 3,276,856 | 10/1966 | Esposito | 71/117 |
| 3,374,083 | 3/1968 | Loux | 71/117 |
| 3,436,405 | 4/1969 | Gasser et al. | 260/343.3 G |

FOREIGN PATENT DOCUMENTS

| | | | |
|---|---|---|---|
| 783611 | 9/1957 | United Kingdom | 71/89 |
| 914893 | 1/1963 | United Kingdom | 71/89 |

OTHER PUBLICATIONS

Grove, "The Gibberellins", (1961), Quarterly Reviews 15, pp. 56–71.
Tamai, "Agents Containing Camphor Oil, etc.;" (1973), CA 79, No. 149273e, (1973).

Primary Examiner—Glennon H. Hollrah
Attorney, Agent, or Firm—Cushman, Darby & Cushman

[57] ABSTRACT

Disclosed are salts of gibberellin with amines which are secondary or tertiary aryl or alkylamines having 16 to 36 carbon atoms, said salts being more effective as plant growth regulants than gibberellin per se and capable of being employed in ultra-low-volume applications.

18 Claims, No Drawings

GIBBERELLIN SALTS

This invention relates to certain gibberellin salts, to compositions containing them and to a method of regulating plant growth using them.

The gibberellins are a group of plant growth regulators derived from cultures of the fungus *Gibberella fujikuroi* (for a description of these substances, see Grove, Quarterly Reviews, 1961, 15, 56–71). The gibberellins include, for example, gibberellin $A_3$ (or gibberellic acid) disclosed in British Patent Specification No. 783,611, gibberellin $A_4$ and gibberellin $A_7$ (the latter being disclosed in British Patent Specification No. 914,893), the disclosures of both these Specifications being incorporated herein by reference. The Specifications also disclose the preparation of ammonium, alkali metal and alkaline earth metal salts of gibberellins $A_3$ and $A_7$.

Gibberellin $A_7$ is obtained commercially as a mixture with a varying (e.g. an equal) proportion of gibberellin $A_4$, in which form it is generally used for plant growth regulating purposes. Gibberellins $A_3$ and $A_4/A_7$ are conveniently applied to plants in the form of compositions in which the active ingredient is mixed with a diluent or carrier. Examples of such compositions include aqueous solutions, and solutions in organic solvents.

Gibberellins are effective at low rates of application. However, they have to be made by slow and difficult fermentation methods, and are in consequence expensive. We have now discovered a way of applying gibberellins which, for some purposes at least, enables a lower rate of application to be used effectively with a consequent saving in cost. The application of reduced volumes of liquid becomes possible and this is of particular value where aerial spraying is used.

The invention provides a salt of a gibberellin with an amine having at least 8, for example 8 to 40, carbon atoms. It also provides a plant growth regulating composition comprising the gibberellin salt and a carrier, e.g. an organic solvent. Further, the invention provides a method of regulating the growth of a plant, which method comprises applying to the plant, or to the locus of the plant, a composition as defined above at a rate of 0.5 to 50 liters of solution per hectare.

The amine can be a primary, secondary or tertiary amine in which the nitrogen atom may be attached to an aliphatic, alicyclic, aromatic or heterocyclic residue and may itself form part of a heterocyclic ring. The amine can be an alkylamine or arylamine. Preferred amines have 16 to 36 carbon atoms; conveniently they are secondary or tertiary alkylamines, for example trinonylamine, disoyaamine, dicocoamine and dimethylcocoamine. Dicocoamine is a commercially available mixture of secondary alkylamines manufactured from the mixed fatty acids of coconut oil, the bulk of the mixed alkylamines having $C_{12}$, $C_{14}$ or $C_{16}$ alkyl moieties. Examples of suitable arylamines are diphenylamine, m-toluidine, aniline and N-methylaniline.

The gibberellin is suitably gibberellin $A_1$, gibberellin $A_3$, gibberellin $A_9$, gibberellin $A_4$, gibberellin $A_7$ or a mixture of gibberellin $A_4$ and gibberellin $A_7$.

The salts may be prepared by reacting (for example at room temperature (17° C. to 70° C. and for up to 1 hour) the gibberellin with the amine, for example (a) by dissolving the gibberellin in a suitable solvent, e.g. methanol, with gentle heating if required, separately dissolving the amine in a suitable solvent (e.g. methanol or chloroform), mixing the two solutions, and evaporating the mixture to dryness, or (b) by dissolving the amine in a solvent such as methylene chloride, mixing with stirring the gibberellin in solid form with the solution and evaporating the mixture to dryness. The evaporation is preferably performed under relatively low pressure (by about 0.1 Torr) since otherwise the salt is obtained in a rather waxy and sticky form.

The compositions can be of two kinds: concentrates suitable for sale to the user, and more dilute formulations which are generally prepared by the user shortly before he applies them to the plants. The concentrates conveniently comprise a solution of 0.1 to 30%, for example 1 to 30% and preferably 5 to 20%, of a salt of the invention in an organic solvent, for example an optionally substituted cyclohexanone (e.g. cyclohexanone itself and the monomethylcyclohexanones), isophorone, butanol, vegetable oils (e.g. cotton seed oil) and Aromasol H (a mixture of trimethylbenzenes), and mixtures thereof with polyethylene glycol, and optionally a surface active agent. All solvents are not equally suitable for all salts of the invention; some salt/solvent combinations (e.g. those illustrated in the Examples hereafter) are better than others.

The concentrates may be diluted prior to use, e.g. with water and/or a non-phytotoxic organic solvent. The resulting diluate may be in the form of a solution or an emulsion. If they are to be diluted with water, they should contain a surface-active agent to assist in the formation of a homogeneous and stable emulsion. They may be diluted with non-phytotoxic organic solvents, whether or not they contain surface-active agents, to form solutions. The preferred solvents are the vegetable oils, for example olive oil, corn oil, cotton seed oil, castor oil, soya-bean oil and especially groundnut oil, also known as arachis or peanut oil.

Examples of suitable surface-active agents are a condensate of p-nonylphenol with 7 to 8 moles of ethylene oxide (sold as Lissapol NX), a condensate of ethylene oxide with octyl phenol (sold as Lubrol E) and a condensate of ethylene oxide with propylene oxide polymer (sold as Pluronic L61).

It is preferred to apply the compositions to the plants at a rate of 1 to 50, particularly 2 to 10, liters of solution per hectare. This method is an adaptation of the so called ULV (ultra-low volume) application technique. This is a known method of applying insecticides, but has not hitherto found frequent application in the regulation of plant growth.

Previously, plants have usually been sprayed for growth regulation purposes at volumes of 200 to 5,000 liters per hectare, two orders of magnitude greater than the volumes used in the method of the present invention. Advantages of the use of lower spray volumes include lower water use, with less bulky and sometimes less complex spraying apparatus. Spraying can be carried out faster and more economically. Because the volume of spray to be applied is so much lower, it becomes a practical possibility to spray some crops from the air. In some cases, plant uptake of the gibberellins from concentrated solutions is better than from dilute solutions, and sometimes penetration of plant tissue may also be improved; such improvement may be due both to the use of the more concentrated solution and to the liquid solubility of the salts.

The compositions can if desired be sprayed on to plants using the so-called electrodynamic spraying technique. A suitable apparatus for this technique is disclosed in British Patent Application No. 29539/76, the disclosure of which document is incorporated herein by reference.

Rates of application of the gibberellin vary according to the plants being treated and the effect sought thereby. Suitable rates are 5 to 200 grams, for example 10 to 200 grams, of gibberellin salt per hectare, though sometimes amounts as low as 1 gram per hectare may give useful results.

The compositions may additionally comprise other plant growth regulating substances, particularly the auxins (e.g. indol-3-yl-acetic acid, indol-3-yl-butyric acid, 1-naphthylacetic acid and 2-naphthoxyacetic acid), the hormone herbicide such as 2,4-D and 2,4,5-TP, and the cytokinins e.g. kinetin (furfurylaminopurine), benzimidazole, benzyladenine (6-benzylaminopurine) and N,N'-diphenylurea.

The uses of gibberellins in agriculture are numerous and diverse. Both monoctyledenous and dicotyledenous plants may be treated. The following are among the crops which have been treated with gibberellins to obtain a variety of useful effects: pears, grapes, rhubarb, oil-palm, oranges, watercress, artichokes, bananas, tea, coffee, sugar-cane and pasture grass (e.g. Pangola grass or Kikuyu grass). Attention is drawn to the review by Turner, Outlook on Agriculture, 1972, Volume 7, Number 1, pages 14 to 20, and various papers in Outlook on Agriculture, 1976, Volume 9, Number 2, the disclosures of which documents are incorporated herein by reference.

There now follows a list of examples of the effects that gibberellins can have on plants.

(1) Increasing vegetative growth particularly on plants under low temperature constraint (examples of plants where this effect can be noticed are the pasture grasses), (2) Breaking of vegetative dormancy (tea, pasture grasses), (3) Modifying flowering and fruiting patterns (coffee, citrus fruits, conifer seed production), (4) Improving fruit setting, e.g. increasing parthenocarpic setting (citrus fruits, pears, apples, grapes), (5) Delaying ripening and senescence (citrus fruits, bananas, tomatoes), and (6) Improving fruit development (seedless grapes).

The following Examples illustrate the invention. All parts and percentages are by weight and all temperatures degrees Centigrade, except where otherwise stated.

EXAMPLE 1

Gibberellin $A_3$ (1 mole) was dissolved in warm methanol. Trinonylamine (1 mole) was dissolved in chloroform. The solutions were mixed. The solvents were evaporated from the resulting mixture and the residue dried to give the trinonylamine salt (yield 95%), m.p. 102°–106°.

EXAMPLE 2

Example 1 was repeated, substituting Armeen 2HT for trinonylamine. Armeen 2HT is a commercially available mixture of secondary amines derived from hydrogenated tallow fats, containing principally the alkyl radicals $C_{16}H_{33}$ and $C_{18}H_{37}$. The Armeen 2HT salt, m.p. 60°–75°, was prepared in 95% yield.

EXAMPLE 3

This Example illustrates the preparation of the Armeen 2C salt of gibberellin $A_3$. Armeen 2C is a commercially available mixture of secondary alkyl amines derived from coconut oil, containing principally $C_{12}H_{25}$, lesser amounts of $C_{14}H_{29}$ and minor amounts of higher alkyl moieties up to $C_{18}$.

Gibberellin $A_3$ (1 mole) was dissolved in warm methanol to give a 5% solution. Armeen 2C (1 mole based on its quoted average molecular weight of 390) was dissolved in methanol to give a 5% solution. The solutions were combined and the methanol removed by evaporation to give the salt (yield 95%), m.p. 80°–85°.

EXAMPLE 4

The following concentrate was prepared.

| | |
|---|---|
| Salt of Example 1 | 21.5% |
| Lissapol NX | 10.0% |
| Sextone B (mixture of monomethylcyclo hexanones, technical grade) | 68.5% |

EXAMPLE 5

The following emulsifiable concentrate was prepared.

| | |
|---|---|
| Salt mixture of Example 2 | 12.2% |
| Lubrol E | 5.0% |
| Aromasol H | 82.8% |

EXAMPLE 6

This Example illustrates a concentrate suitable for use, after dilution with vegetable oil for spraying on plants.

| | |
|---|---|
| Salt of Example 3 | 10.48% |
| Cyclohexanone | 44.76% |
| Polyethylene glycol (mean molecular weight 200) | 44.76% |

The specific gravity of the concentrate is 1.038.

EXAMPLE 7

This Example illustrates a composition suitable for use by the electrodynamic spraying technique.

The following concentrate was prepared.

| | |
|---|---|
| Salt of Example 3 | 0.214% |
| Cyclohexanone | 20% |
| N-methylpyrrolidone | 20% |
| Cotton seed oil | up to 100% |

This concentrate was diluted with a mixture of N-methylpyrrolidone (20%), Isopar L (an isoparaffin solvent; 17.4%) and cotton seed oil (to 100%) to give a composition containing varying amounts (0.1 to 100 p.p.m.) of gibberellin.

Examples 8 and 9 illustrate the method of the invention applied to oranges.

Growers frequently spray Navel orange fruits with gibberellin $A_3$ ($GA_3$) to improve skin quality and delay ripening. Such treatment results in a firmer rind which is less liable to mechanical damage and causes a delay both in rind colouring and the onset of rind puffiness and other physiological degenerative conditions. This results in improved quality in fruits picked late in the harvesting season.

EXAMPLE 8

Trees of a variety of early Navel orange (Thompsons Navel) in Valencia, Spain, bearing fruits at an early stage of ripening (the rinds were just turning from green to yellow) were sprayed with $GA_3$ at a rate equivalent to 100 g/ha. The compound was formulated in two ways: Formulation A for purposes of comparison and Formulation B according to the invention.

Formulation A

Solid pure $GA_3$ was dissolved in a little acetone/ethanol, adding water to form an aqueous solution. Alkylphenol/polyoxyethylene condensate wetter was added to the water so that when the $GA_3$ solution was made up to final volume the concentration of wetter was 0.1%.

Formulation B

An appropriate quantity of the emulsifiable concentrate of Example 5 was diluted with olive oil to make up the volume to the quantity required for spraying.

Both formulations were each applied to six separate orange trees with a low volume spray applicator at a volume equivalent to 20 liters/ha and in a manner which ensured dispersion of the fine spray droplets over the foliage and fruits on the full circumference of each tree. The fruits on 12 other trees were retained untreated as controls. Treatments and controls were sprayed onto trees in a randomised block experimental design.

99 Days after spraying, fruits were picked from treated and control trees. A measure of the skin hardness of 10 fruits taken at random from each replicate tree was obtained by a penetrometer test which measures the force in grams needed to push a standard needle at constant speed through the rind of each orange at one spot on the equator. The results in Table I show that the rinds of oranges treated with each Formulation were significantly harder than the rinds of control fruits, but that the fruits treated with Formulation B had significantly harder skins than the skins of fruits treated with Formulation A.

TABLE 1

| TREATMENT | PENETROMETER READING (g) |
|---|---|
| Formulation A (100 g/l of $GA_3$) | 312 |
| Formulation B (100 g/l of $GA_3$) | 361 |
| Control, untreated fruits | 269 |

EXAMPLE 9

In another experiment conducted in Spain, Washington Navel Orange trees were sprayed with $GA_3$ formulations just before the fruits were expected to ripen and change colour from green to orange. The $GA_3$ was applied at rates equivalent to 40 and 80 g/ha. Three $GA_3$ formulations were used. Formulations A and B of Example 8 and

Formulation C an appropriate quantity of the 10% emulsifiable concentrate formulation described in Example 4 was treated with olive oil to make up the volume to the quantity required for spraying.

Formulation A was sprayed on 6 trees at 40 g/ha and at 80 g/ha of $GA_3$ in a volume equivalent to 2000 liters/ha. High volume sprays of aqueous preparations of $GA_3$ such as this are normally used by citrus growers for treating Navel orange fruits.

Sprays of $GA_3$ were also applied at 20 liters/ha. For these applications, Formulations A and B (sprayed at 40 g/ha and 80 g/ha) and Formulation C (sprayed at 80 g/ha) were used. Each treatment was applied to the foliage and fruits on 6 separate orange trees.

Both high and low volume applications, together with the other treatments, were arranged in a randomised block design in which there were 12 untreated control trees.

48 Days and 103 days after the trees were sprayed, 40 fruits were picked at random from each of the treated control trees. The colour of each fruit was assessed and recorded on the following scale.
1 = orange
2 = orange-yellow
3 = yellow
4 = yellow with a green tinge
5 = midway between yellow and green The average colour grades of each of the experimental treatments is given in Table 2 below.

These results show that at both harvest dates, Formulation B sprayed at 40 g/ha and 20 l/ha caused the rinds of Navel orange fruits to be significantly yellower in colour (indicating delayed skin ripening) than the rinds of fruits treated with Formulation A at 40 or 80 g/ha and at 2000 l/ha.

At the second harvest, Formulations B and C gave significantly paler coloured fruits than equivalent rates of aqueous $GA_3$ applied at 20 g/ha or 2000 l/ha.

Formulation B applied at 40 g/ha and 20 l/ha gave results at both harvests equivalent or significantly superior to the results obtained by applications of aqueous $GA_3$ at double the rate per hectare applied at 20 or 2000 l/ha.

TABLE 2

| FORMULATION | RATES | | MEAN COLOUR GRADES | |
|---|---|---|---|---|
| | l/ha | g/ha OF $GA_3$ | After 48 DAYS | After 103 DAYS |
| Formulation A | 2000 | 40 | 3.25 | 2.11 |
| Formulation A | 2000 | 80 | 3.18 | 2.14 |
| Formulation A | 20 | 40 | 3.38 | 2.10 |
| Formulation A | 20 | 80 | 3.55 | 2.21 |
| Formulation B | 20 | 40 | 3.75 | 2.28 |
| Formulation B | 20 | 80 | 3.83 | 2.46 |
| Formulation C | 20 | 80 | 3.90 | 2.47 |
| Untreated controls | — | — | 2.16 | 1.89 |

EXAMPLE 10

This Example illustrates the treatment of monocotyledonous plants to increase rate of growth, and the increased effects obtainable with the compositions of the invention as compared with known compositions.

Dwarf maize (Zea mays; variety D5, an F1 hybrid) was grown in pots in the glasshouse. There were two treatments, D and E, and an untreated control, each with five replicate plants. For treatment D, $GA_3$ tablets were dissolved in water with the addition of 0.025% w/v alkylphenol/polyoxyethylene condensate wetter, to give a solution containing 10 p.p.m. $GA_3$. This was applied to the maize through a standard spraying nozzle at a rate equivalent to 500 l/ha, giving a calculated application rate per plant of 0.5 μg $GA_3$. For treatment E, the formulation of Example 6 was dissolved in groundnut oil to give a solution containing 1000 p.p.m. $GA_3$. This was applied to the maize by a spinning disc applicator at 10 l/ha giving a calculated application rate per plant of 0.51 μg $GA_3$. The gibberellin response of the maize plants was assessed by measuring the first internode (distance between first and second ligule) 6, 8 and 13 days after spraying. The results in Table 3 show notably greater activity for treatment E according to the invention than treatment D according to the prior art. At 6 days, plants treated by treatment E also showed the second internode. This did not appear in the other plants until 8 days. No treatment showed any phytotoxicity or other abnormality.

TABLE 3

| | Mean Internode Length (mm) | | |
|---|---|---|---|
| Days After Treatment | Control | Treatment D | Treatment E |
| 6 | 7.2 | 9.2 | 23.6 |
| 8 | 8.0 | 11.6 | 25.6 |
| 13 | 11.4 | 15.8 | 29.2 |

EXAMPLE 11

This Example illustrates the increased effects obtained with the salts of the invention on a monocotyledonous plant growing under field conditions.

It is well known that the growth of some tropical pasture grasses is greatly reduced by low night temperatures and that such reductions can be partly overcome by the application of gibberellic acid (Whitney, Agronomy J., 1976, 68, 365–370, the disclosure of which document is incorporated herein by reference).

Comparative tests were conducted on farm pastures of pangola grass (*Digitaria decumbens*) at two locations in Florida, USA. Treatments were performed in November when growth was retarded. Gibberellic acid was formulated in two ways. Formulation A for purposes of comparison and Formulation B according to the invention.

Formulation A $GA_3$ as the water soluble commercial formulation 'Berelex' was dissolved in water to give solutions of the required concentrations. Alkylphenol/polyoxyethylene condensate wetter was added to the water to give a concentration of 0.1% in the final volume.

Formulation B

Appropriate quantities of the concentrate of Example 6 was diluted with corn oil to give solutions of the required concentrations.

Both formulations were applied at three different concentrations. In all cases, Formulation A was applied in a volume equivalent to 500 liters/hectare while Formulation B was applied in a volume equivalent of 5 liters/hectare. Each treatment was applied to six replicate plots each 39 $m^2$ in area. Treatment and control plots were distributed in a random block experimental design. Before treatment, all the plots were mowed to a uniform height and dressed with ammonium nitrate fertiliser at a rate equivalent to 56 kg/hectare.

36 Days after spraying the plots were mowed and the fresh weight of the clippings determined.

The results in Table 4 show that on site 1 Formulation B was at least three times as effective as Formulation A. On site 2 Formulation B was about 1.5 times as effective as Formulation A.

TABLE 4

| FRESH WEIGHT YIELD OF PANGOLA GRASS | | | | |
|---|---|---|---|---|
| | SITE 1 | | SITE 2 | |
| TREATMENT | kg/$m^2$ | % | kg/$m^2$ | % |
| Formulation A 24 g/ha | 0.246 | 120 | 0.610 | 147 |
| Formulation A 48 g/ha | 0.327 | 159 | 0.688 | 165 |
| Formulation A 96 g/ha | 0.359 | 175 | 0.852 | 205 |
| Formulation B 12 g/ha | 0.307 | 150 | 0.636 | 153 |
| Formulation B 24 g/ha | 0.344 | 167 | 0.665 | 160 |
| Formulation B 48 g/ha | 0.455 | 221 | 0.770 | 185 |
| Control | 0.206 | 100 | 0.416 | 100 |

EXAMPLE 12

This Example illustrates the application to tomatoes of the diphenylamine and trinonylamine salts of gibberellic acid as low volume sprays in groundnut oil.

The diphenylamine and trinonylamine salts of $GA_3$ were prepared as solutions in propylene glycol containing 5% w/v $GA_3$ equivalent. These solutions were formulated in groundnut oil as secondary carrier to give solutions containing active ingredient at the equivalent of 150 and 350 μg/ml of $GA_3$. They were sprayed onto tomato plants at a volume equivalent to 10 l/ha, using an Aerograph Super 63 air brush, model E-504, at 2.0 atmospheres. This is equivalent to 15 and 35 g/ha of $GA_3$. These treatments were compared with treatments using solutions of $GA_3$ prepared by dissolving the requisite amounts of $GA_3$ in a few drops of ethanol and then further diluting the solution with larger volumes of water to give preparations containing 1.5 and 3.5 μg/ml of $GA_3$. These aqueous formulations were sprayed at 1000 l/ha using an Aerograph DeVilbiss Type MPS spray gun at 1.4 atmospheres.

The tomatoes (variety Sutton's "Best of All") used for the experiment were propagated in 10 cm diameter plastic pots using a peat/sand compost. Ten such plants were used per treatment; 10 untreated plants were used as controls. They were sprayed at 35 days after sowing. Plants were arranged randomly within blocks, one replicate of each treatment per block. The stem length of each plant was measured from the cotyledons to the growing point immediately prior to spraying and again 7 days afterwards. The results in Table 5 show increases in stem length over this 7 day period for treated and untreated plants. Greater increases in stem length were obtained by spraying $GA_3$ in the form of the amine salts in oil, rather than as the free acid in water.

TABLE 5

| | Height Increase (mm)At | |
|---|---|---|
| | 15 g/ha | 35 g/ha |
| Diphenylamine salt in propylene glycol + groundnut oil | 55 | 66 |
| Trinonylamine salt in propylene glycol + groundnut oil | 62 | 72 |
| $GA_3$ free acid in dilute aqueous ethanol* | 47 | 53 |
| Untreated control | 40 | |

Least significant difference between treatment means:
$P = 0.05 : 6.0$
$P = 0.01 : 7.9$
*The addition of a wetter to this composition could improve the height increase figures.

We claim:

1. A salt of a gibberellin with an amine which is a secondary or tertiary arylamine or alkylamine having 16 to 36 carbon atoms, said gibberellin being selected from the group consisting of gibberellin $A_1$, gibberellin $A_3$, gibberellin $A_9$, gibberellin $A_4$, gibberellin $A_7$ and a mixture of gibberellin $A_4$ and gibberellin $A_7$, said salt being effective for regulating plant growth at a lower application rate than the parent gibberellin.

2. A salt as claimed in claim 1 wherein the amine is trinonylamine, disoyaamine, dicocoamine or dimethylcocoamine.

3. A salt as claimed in claim 1 wherein the amine is diphenylamine.

4. A salt of a gibberellin with an amine which is a secondary or tertiary alkylamine having 16 to 36 carbon atoms.

5. A composition suitable for regulating the growth of plants, the composition consisting essentially of (a) a plant growth regulating effective amount of a salt as claimed in claim 1, (b) a carrier which is water or at least one organic solvent and optionally (c) a surface active agent.

6. A composition as claimed in claim 5 wherein the salt is formed from trinonylamine, disoyaamine, dicocoamine or dimethylcocoamine.

7. A composition as claimed in claim 5 wherein the salt is formed from diphenylamine.

8. A composition suitable after dilution for regulating the growth of plants, the composition consisting essentially of (a) 0.1 to 30% by weight of the salt as claimed in claim 1, the salt being dissolved in at least one organic solvent, and optionally (b) a surface active agent.

9. A composition as claimed in claim 8 wherein the salt is formed from trinonylamine, disoyaamine, dicocoamine, or dimethylcocoamine.

10. A composition as claimed in claim 8 wherein the salt is formed from diphenylamine.

11. A composition as claimed in claim 8 which contains 5 to 20% by weight of the salt.

12. A composition suitable for regulating the growth of plants, the composition consisting essentially of (a) a plant growth regulating effective amount of a salt as claimed in claim 4, (b) a carrier which is water or at least one organic solvent and optionally (c) a surface active agent.

13. In a method of regulating the growth of a plant using a gibberellin, the improvement consisting essentially of the step of applying to the plant, or to the locus of the plant, a plant growth regulating effective amount of a composition as claimed in claim 5.

14. In a method of regulating the growth of a plant using a gibberellin, the improvement consisting essentially of the step of applying to the plant, or to the locus of the plant, a plant growth regulating effective amount of a composition as claimed in claim 6.

15. In a method of regulating the growth of a plant using a gibberellin, the improvement consisting essentially of the step of applying to the plant, or to the locus of the plant, a plant growth regulating effective amount of a composition as claimed in claim 7.

16. A method as claimed in claim 13 wherein the composition is applied at a rate of 1 to 50 liters per hectare.

17. A method as claimed in claim 16 wherein the composition is applied at a rate of 2 to 10 liters per hectare.

18. In a method of regulating the growth of a plant using a gibberellin, the improvement consisting essentially of the step of applying to the plant, or to the locus of the plant, a plant growth regulating effective amount of a composition as claimed in claim 12.

* * * * *